(12) United States Patent
Lim

(10) Patent No.: US 11,475,663 B2
(45) Date of Patent: Oct. 18, 2022

(54) VISUAL AID DEVICE AND VISUAL AID METHOD BY WHICH USER USES VISUAL AID DEVICE

(71) Applicant: SAMSUNG LIFE PUBLIC WELFARE FOUNDATION, Seoul (KR)

(72) Inventor: Dong Hui Lim, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 9 days.

(21) Appl. No.: 17/059,368

(22) PCT Filed: May 28, 2019

(86) PCT No.: PCT/KR2019/006393
§ 371 (c)(1),
(2) Date: Jan. 20, 2021

(87) PCT Pub. No.: WO2019/231216
PCT Pub. Date: Dec. 5, 2019

(65) Prior Publication Data
US 2021/0240988 A1    Aug. 5, 2021

(30) Foreign Application Priority Data
May 28, 2018  (KR) .................. 10-2018-0060436

(51) Int. Cl.
*G06V 20/20* (2022.01)
*G06N 20/00* (2019.01)
(Continued)

(52) U.S. Cl.
CPC ............ *G06V 20/20* (2022.01); *A61F 9/08* (2013.01); *G06K 9/6267* (2013.01); *G06N 3/08* (2013.01);
(Continued)

(58) Field of Classification Search
CPC ........ G06V 20/20; G06V 10/40; G06V 10/82; G06V 20/41; G06V 20/46; A61F 9/08;
(Continued)

(56) References Cited

U.S. PATENT DOCUMENTS

| | | | | |
|---|---|---|---|---|
| 10,860,100 B2 * | 12/2020 | Osterhout | ............... | G06F 1/163 |
| 2013/0214998 A1 * | 8/2013 | Andes | ...................... | G09G 5/10 345/8 |
| 2017/0249863 A1 * | 8/2017 | Murgia | .................. | G02C 11/10 |

FOREIGN PATENT DOCUMENTS

| | | | |
|---|---|---|---|
| JP | 2000-325389 A | 11/2000 | |
| JP | 2001-318347 A | 11/2001 | |

(Continued)

OTHER PUBLICATIONS

Search Report issued in International Application No. PCT/KR2019/006393, dated Sep. 9, 2019, 2 pages.

(Continued)

*Primary Examiner* — Michael E Teitelbaum
(74) *Attorney, Agent, or Firm* — Dilworth IP, LLC

(57) ABSTRACT

A vision assistance apparatus may include an image acquisition unit configured to acquire an image by capturing the scene of the front which a user watches, a sensor unit configured to acquire sensing information on objects located in front of the user, a control unit configured to analyze the image acquired by the image acquisition unit and generate a notification signal for the front scene through an analysis result of the image and the sensing information acquired by the sensor unit, and an output unit configured to provide the user with the notification signal generated by the control unit in the form of sound.

8 Claims, 12 Drawing Sheets

(51) Int. Cl.
  *A61F 9/08* (2006.01)
  *G06K 9/62* (2022.01)
  *G06N 3/08* (2006.01)
  *G08B 21/18* (2006.01)
  *H04N 5/262* (2006.01)
  *H04N 5/272* (2006.01)
  *H04N 5/45* (2011.01)
  *H04N 5/57* (2006.01)
  *G06V 10/40* (2022.01)

(52) U.S. Cl.
  CPC .............. *G06N 20/00* (2019.01); *G06V 10/40* (2022.01); *G08B 21/18* (2013.01); *H04N 5/2628* (2013.01); *H04N 5/272* (2013.01); *H04N 5/45* (2013.01); *H04N 5/57* (2013.01)

(58) Field of Classification Search
  CPC ........ G06K 9/6267; G06N 3/08; G06N 20/00; G06N 3/0454; G08B 21/18; G08B 13/19613; G08B 1/08; G08B 21/02; H04N 5/2628; H04N 5/272; H04N 5/45; H04N 5/57; H04N 7/18; G09B 21/008; G02B 27/01; G02B 27/017; G02B 2027/0138; G02B 2027/0178
  See application file for complete search history.

(56) References Cited

FOREIGN PATENT DOCUMENTS

| | | | |
|---|---|---|---|
| JP | 2002-065721 | A | 3/2002 |
| KR | 1020060071507 | A | 6/2006 |
| KR | 1020120059281 | A | 6/2012 |
| KR | 10-2012-0059753 | A | 2/2013 |
| KR | 1020140145091 | A | 12/2014 |
| KR | 1020160028305 | A | 3/2016 |
| KR | 1020160117807 | A | 10/2016 |

OTHER PUBLICATIONS

Notice of Allowance from KR Application No. 10-2018-0060436 dated Aug. 10, 2021.
Office Action from KR Application No. 10-2018-0060436 dated Feb. 5, 2021, 6 pages.

* cited by examiner

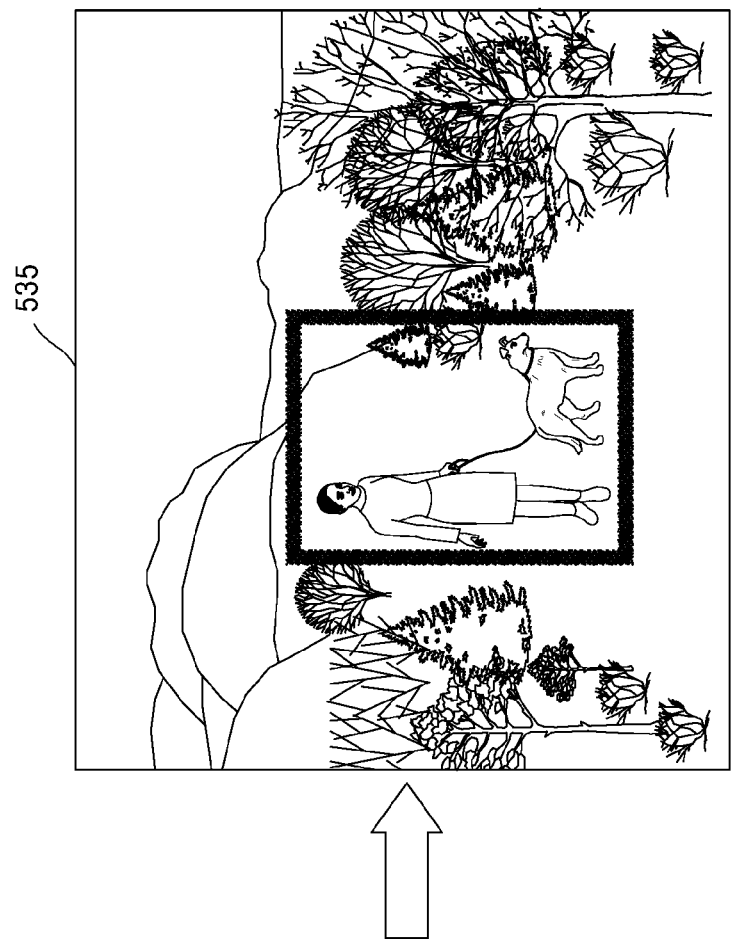
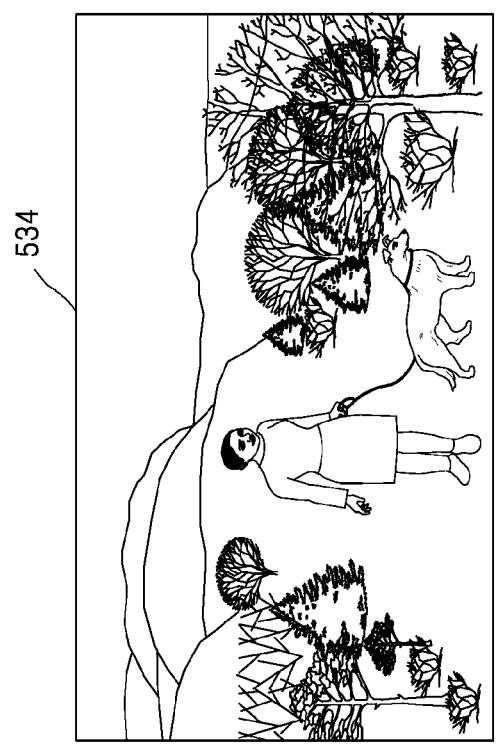
FIG. 10

VISUAL AID DEVICE AND VISUAL AID METHOD BY WHICH USER USES VISUAL AID DEVICE

FIELD OF THE INVENTION

The present disclosure relates to a vision assistance apparatus and a vision assistance method for a user using the same, and more particularly, to a vision assistance apparatus in which an image obtained by capturing a scene in front of a user is analyzed by executing a learning model for extracting features in the image, and a notification signal is provided to the user based on sensing information measured from objects in front of the user, thereby providing vision assistance for the user, and a vision assistance method using the same.

BACKGROUND OF THE INVENTION

Examples of the visually impaired include both the blind and people with low vision, and the people with low vision have different modalities for each individual. Furthermore, there are various causes of diseases that cause a visual impairment, and the modalities of the visual impairment may be slightly different depending on the standard of living of the society, social environments, changes according to the times, and the like. Particularly, there are various causes of several representative important diseases related to blindness among the types of the visual impairment, and in some cases, such diseases may not be clearly distinguished and thus the causes thereof may not be known.

In the related art, only technologies for vision assistance tools for the blind and people with low vision have been proposed. Even in such technologies, information on a scene in front of a visually impaired person is extracted only through various sensors. Furthermore, even though the scene in front of the visually impaired person is captured, there is a problem in that it is difficult to provide accurate information for the visually impaired person through analysis of the capture image.

In addition, there is an urgent need to develop an assistance apparatus for vision assistance for not only the visually impaired but also patients with various diseases such as glaucoma causing the visual impairment.

Patent Literature 1: Korean Patent Application Laid-Open No. 10-2003-0015936 (Publication Date: Feb. 26, 2003)

SUMMARY OF THE INVENTION

The present disclosure has been made to solve the above problems, and an object of the present disclosure is to propose a vision assistance apparatus for users with various diseases related to a visual impairment as well as the visual impairment, thereby providing optimal vision assistance according to the type of assistance for each user.

Technical objects to be achieved in the present disclosure are not limited to the aforementioned matters, and other unmentioned technical problems may be considered by those skilled in the art to which the present disclosure pertains from the following embodiments of the present disclosure to be described below.

As an embodiment of the present disclosure, a vision assistance apparatus may be provided.

The vision assistance apparatus according to an embodiment of the present disclosure may include: an image acquisition unit configured to acquire an image obtained by capturing the scene of the front which a user watches; a sensor unit configured to acquire sensing information on objects located in front of the user; a control unit configured to analyze the image acquired by the image acquisition unit and generate a notification signal for the front scene through an analysis result of the image and the sensing information acquired by the sensor unit; and an output unit configured to provide the user with the notification signal generated by the control unit in the form of sound, wherein the control unit may execute a predetermined learning model for extracting features from the acquired image, and analyze the image by classifying the objects in the front scene on the basis of the features extracted using the learning model.

The vision assistance apparatus according to an embodiment of the present disclosure may further include a display unit configured to output an auxiliary image for vision assistance of the user generated by correcting the image acquired by the image acquisition unit.

The vision assistance apparatus according to an embodiment of the present disclosure may further include a mode selection unit configured to select an operation mode according to the user.

The operation mode of the vision assistance apparatus according to an embodiment of the present disclosure may include a total blindness mode, and in a case where the total blindness mode is selected as the operation mode, the sensor unit may measure a distance value from the object to the user, and when the control unit determines that the measured distance value is within a predetermined reference value, the notification signal may be outputted through the output unit.

The operation mode of the vision assistance apparatus according to an embodiment of the present disclosure may include a low vision mode, and when the low vision mode is selected as the operation mode, the display unit may output the auxiliary image generated by adjusting at least one of contrast data, color data, focus data, brightness data, and size data of the acquired image.

The operation mode of the vision assistance apparatus according to an embodiment of the present disclosure may include a glaucoma mode, and when the glaucoma mode is selected as the operation mode, the image acquisition unit may acquire a fish-eye image captured by a fish-eye lens, and the display unit may output the auxiliary image formed by remapping the fish-eye image into tunnel vision of the user.

The operation mode of the vision assistance apparatus according to an embodiment of the present disclosure may include a macular hole mode, and when the macular hole mode is selected as the operation mode, the display unit may output the auxiliary image formed by allowing a part deficient due to a dark spot generated in a center of the visual field of the user to be separately displayed on a peripheral part adjacent to the center of the visual field of the user.

The operation mode of the vision assistance apparatus according to an embodiment of the present disclosure may include a strabismus mode, and when the strabismus mode is selected as the operation mode, the auxiliary image may include a first auxiliary image for a left eye of the user and a second auxiliary image for a right eye of the user, and the display unit may output the first auxiliary image and the second auxiliary image formed by shifting the image acquired by the image acquisition unit, on the basis of a viewing angle of the left eye of the user and a viewing angle of the right eye of the user.

The operation mode of the vision assistance apparatus according to an embodiment of the present disclosure may include an auditory assistance mode, and when the auditory assistance mode is selected as the operation mode, the control unit may generate an image signal for the object by analyzing sound information from the object acquired by the sensor unit, and the auxiliary image formed by allowing the image signal generated by the control unit to be displayed on the image acquired by the image acquisition unit may be outputted through the display unit.

A vision assistance method for a user using the vision assistance apparatus according to an embodiment of the present disclosure may be provided.

The vision assistance method for a user using the vision assistance apparatus according to an embodiment of the present disclosure may include a step of acquiring an image by capturing the scene of the front which a user watches; a step of acquiring sensing information on objects located in front of the user; a step of analyzing the acquired image; a step of generating a notification signal for the front scene through an analysis result of the acquired image and the acquired sensing information; and a step of providing the user with the generated notification signal in the form of sound, wherein the step of analyzing the acquired image may include: a step of executing a predetermined learning model to extract features of the acquired image; and a step of classifying objects in the front scene on the basis of the extracted features.

In the vision assistance method for a user using the vision assistance apparatus according to an embodiment of the present disclosure, a step of selecting an operation mode according to the user may be performed before execution of the step of generating a notification signal for the front scene through an analysis result of the acquired image and the acquired sensing information, and a step of displaying an auxiliary image for vision assistance for the user, which is generated by correcting the acquired image, may be performed together with the step of providing the generated notification signal to the user in the form of sound.

Meanwhile, as an embodiment of the present disclosure, a computer-readable recording medium, on which a program for implementing the aforementioned method is recorded, may be provided.

According to the present disclosure described above, it is possible to provide an optima vision assistance apparatus for each type to users with a visual impairment and related diseases causing the visual impairment.

Furthermore, an image captured through a machine learning algorithm-based learning model is analyzed, so that information on the scene in front of a user can be accurately determined and a notification signal for vision assistance can be provided.

In addition, a vision assistance apparatus can be manufactured as a vision assistance in the form of a headset or a vision assistance module, which can be attached to other devices, as well as a goggle-type and glasses-type vision assistance apparatus, so that a form of a vision assistance apparatus suitable for a user can be provided.

Effects achievable in the embodiments of the present disclosure are not limited to the aforementioned effects and the other unmentioned effects will be clearly derived and understood by those skilled in the art to which the present disclosure pertains from the description of the following embodiments of the present disclosure. That is, unintended effects according to the implementation of the present disclosure may also be derived by those skilled in the art from the embodiments of the present disclosure.

BRIEF DESCRIPTION OF DRAWINGS

FIG. 10 is an exemplary view illustrating a state in which a fish-eye image of the vision assistance apparatus according to an embodiment of the present disclosure is remapped into a user's tunnel vision.

DETAILED DESCRIPTION OF THE INVENTION

Figure 1:
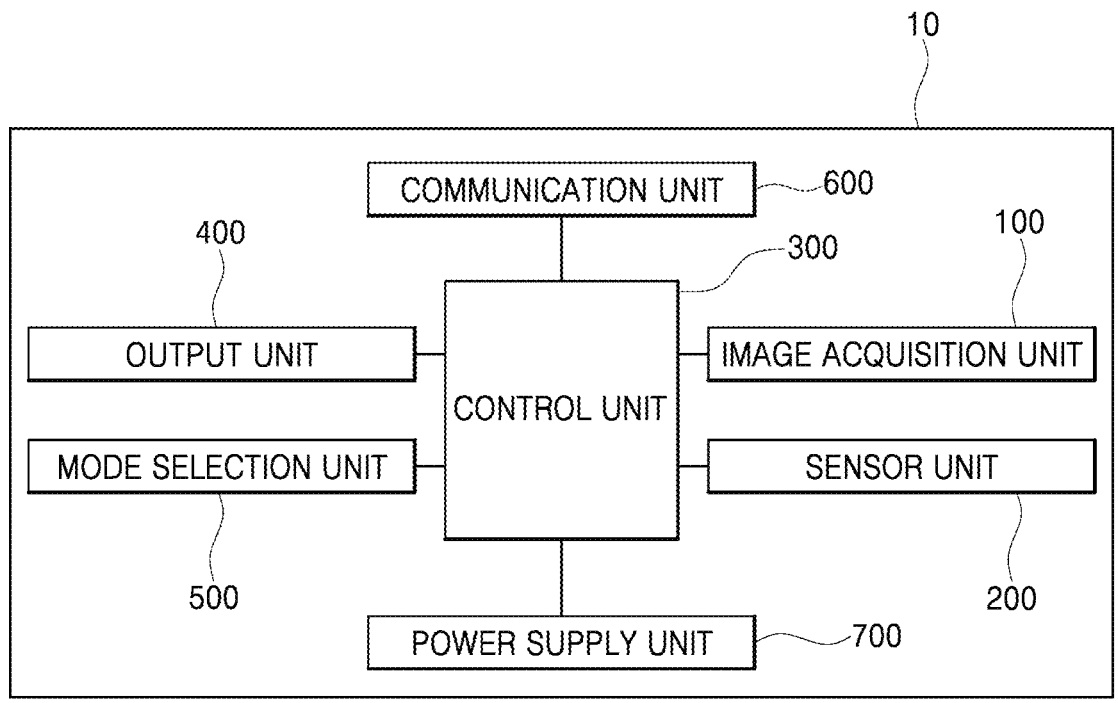
FIG. 1 is a block diagram illustrating a vision assistance apparatus according to an embodiment of the present disclosure.

Hereinafter, embodiments of the present disclosure will be described in detail with reference to the accompanying drawings so as to be easily carried out by those skilled in the art to which the present disclosure pertains. However, the present disclosure can be implemented in various different forms and is not limited to the embodiments described below. In the drawings, parts irrelevant to the description are omitted in order to clearly describe the present disclosure, and similar reference numerals are given to similar parts throughout the specification.

The terms used in the present specification will be briefly described and the present disclosure will be described in detail.

As the terms used in the present disclosure, general terms currently widely used as possible have been selected in consideration of functions in the present disclosure, but the terms may vary depending on the intention of a person skilled in the art, precedent, emergence of new technologies, and the like. Furthermore, in certain cases, some terms are arbitrarily selected by an applicant, and in such a case, meanings of the terms will be described in detail in the corresponding description of the disclosure. Accordingly, the terms used in the present disclosure need to be defined based on the meanings thereof and overall details of the present disclosure, instead of simple names of the terms.

Throughout the specification, when a certain part is referred to as "including" a certain component, it means that the part may not exclude other components but further include other components, unless otherwise stated. Furthermore, a term such as " . . . unit" and " . . . module" described in the specification means a unit for processing at least one function or operation, and this may be implemented with hardware, software, or a combination of the hardware and the software. Furthermore, when a certain part is referred to as being "connected" to another part, it includes not only a case where the part is "directly connected" to the another part but also a case where the part is connected to the another part "with another configuration interposed therebetween".

Hereinafter, the present disclosure will be described in detail with reference to the accompanying drawings.

FIG. 1 is a block diagram illustrating a vision assistance apparatus 10 according to an embodiment of the present disclosure. Referring to FIG. 1, the vision assistance apparatus 10 according to an embodiment of the present disclosure may include an image acquisition unit 100 that acquires an image by capturing the scene in front of a user, a sensor unit 200 that acquires sensing information on objects located in front of the user, a control unit 300 that analyzes the image acquired by the image acquisition unit 100 and generates a notification signal for the front scene through an analysis result of the image and the sensing information acquired by the sensor unit 200, and an output unit 400 that provides the user with the notification signal generated by the control unit 300 in the form of sound. Furthermore, according to an embodiment, the vision assistance apparatus 10 may further include a power supply unit 700 for supplying power to the vision assistance apparatus 10.

The image acquisition unit 100 of the vision assistance apparatus 10 according to an embodiment of the present disclosure may include at least one capturing module for capturing the scene in front of the user and a storage module for storing the image captured by the capturing module. The capturing module of the image acquisition unit 100 may be located around the left eye and the right eye of the user so as to capture the scene that the left eye and the right eye of the user watches. The capturing module may capture the scene in front of the user through a sensor such as a charge-coupled device (CCD) and a complementary metal oxide semiconductor (CMOS).

The sensor unit 200 of the vision assistance apparatus 10 according to an embodiment of the present disclosure may include at least one of an object detection module 210 capable of detecting an object located around the user, a distance measurement module 230 capable of measuring a distance to an obstacle located in front of the user, a location measurement module 220 capable of measuring a current location of the user, and a speed measurement module capable of measuring a movement speed of the user. That is, the sensor unit 200 may include all sensor modules capable of acquiring information on an object or an obstacle located around the user. The object detection module 210 may include at least one of an infrared sensor, a proximity sensor, an ultrasonic sensor, and a motion sensor. The distance measurement module 230 may include at least one of an infrared sensor, an ultrasonic sensor, a light detection and ranging (LIDAR) sensor, and a radio detection and ranging (RADAR) sensor. The location measurement module 220 may include at least one of a global positioning system (GPS) module, a wireless fidelity (WiFi) module, and an inertial measurement module. The speed measurement module may include at least one of an acceleration sensor, a Gyro sensor, and an inertial measurement module. Each of the sensor modules may further include a control circuit for controlling at least one sensor included therein.

The control unit 300 of the vision assistance apparatus 10 according to an embodiment of the present disclosure may analyze the image acquired by the image acquisition unit 100 and generate the notification signal for the front scene through the analysis result of the image and the sensing information acquired by the sensor unit 200. The control unit 300 may execute a predetermined learning model for extracting features from the acquired image, and analyze the image by classifying the objects in the front scene on the basis of the features extracted using the learning model.

The control unit 300 controls the overall operation of the vision assistance apparatus 10 in addition to the operation of generating the notification signal as described above. That is, as illustrated in FIG. 1, the image acquisition unit 100, the sensor unit 200, the output unit 400, a mode selection unit 500, the power supply unit 700, and a communication unit 600 are connected through the control unit 300, so that the control unit 300 may control at least a part of the components. In addition, in the control unit 300, at least two or more of the components included in the vision assistance apparatus 10 may operate in combination with each other for the operation of the vision assistance apparatus 10.

The output unit 400 of the vision assistance apparatus 10 according to an embodiment of the present disclosure may provide the notification signal for vision assistance for a user, which is generated by the control unit 300, in the form of sound. The output unit 400 may be located around at least one of the left ear and the right ear of the user, thereby allowing the user to easily recognize vision assistance information.

The sound of the notification signal provided by the output unit 400 may be preset by the user, and sound setting may be changed through cooperation with a user device 30. There is no limitation in the sound that may be preset by the user, but the user may select sound as the notification signal appropriate to the user himself/herself. For example, the notification signal may be provided through the voice of a person familiar to the user himself/herself or an entertainer who the user himself/herself likes. Furthermore, the notification signal may be provided as various patterns of alarm sounds by setting a sound providing period differently according to the scene in front of the user and providing the notification signal. In addition, when the sound is provided in the form of voice, the voice may be provided in various languages such as English, Japanese, and Chinese as well as Korean.

The power supply unit 700 of the vision assistance apparatus 10 according to an embodiment of the present disclosure may supply power for the operation of the vision assistance apparatus 10. That is, the components of the vision assistance apparatus 10 may operate through the supply of power by the power supply unit 700.

Figure 2:
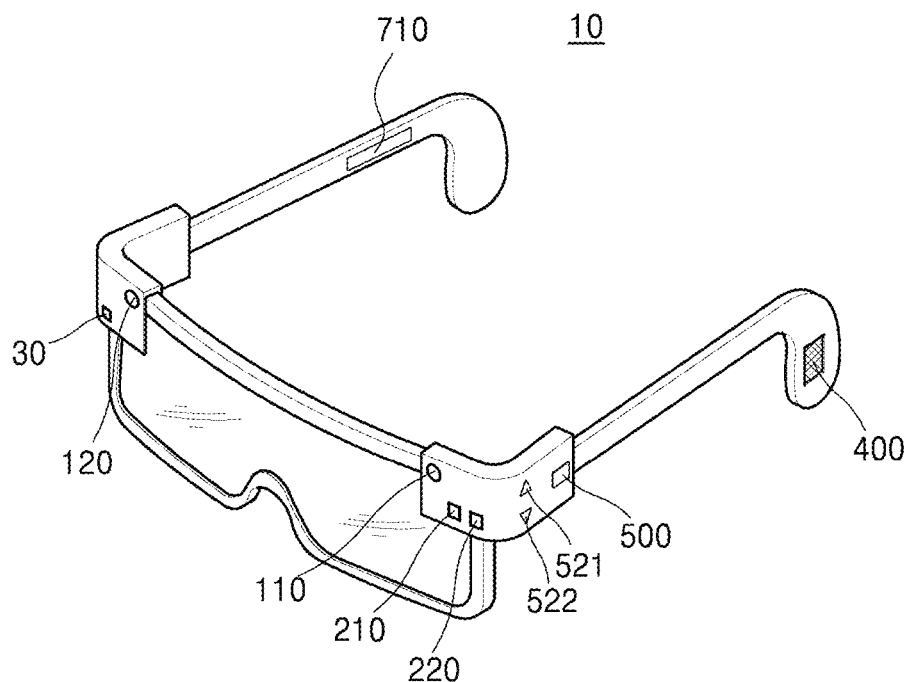
FIG. 2 is an exemplary view illustrating a goggle-type vision assistance apparatus according to an embodiment of the present disclosure.

The power supply unit 700 may be formed in various forms including a power supply device. As illustrated in FIG. 2, a power switch 710 is attached, so that whether to supply power may be adjusted according to whether the vision assistance apparatus 10 is detached from the user. For example, the power switch 710 may include a touch detection sensor module using a capacitive touch sensor or a resistive touch sensor, and allow power to be supplied when the user wears the vision assistance apparatus 10 and to stop the supply of power when the user takes off the vision assistance apparatus 10.

Furthermore, the image capturing in the image acquisition unit 100 may be adjusted through the control unit 300 according to the operation of the power switch 710. Specifically, when the user wears the vision assistance apparatus 10, the power switch 710 comes into contact with the head of the user, so that an image may be captured by the capturing module of the image acquisition unit 100. When the user takes off the vision assistance apparatus 10, the power switch 710 is detached from the head of the user and the supply of power by the power supply unit 700 is stopped, so that image capturing by the image acquisition unit 100 may be stopped.

Figure 3:
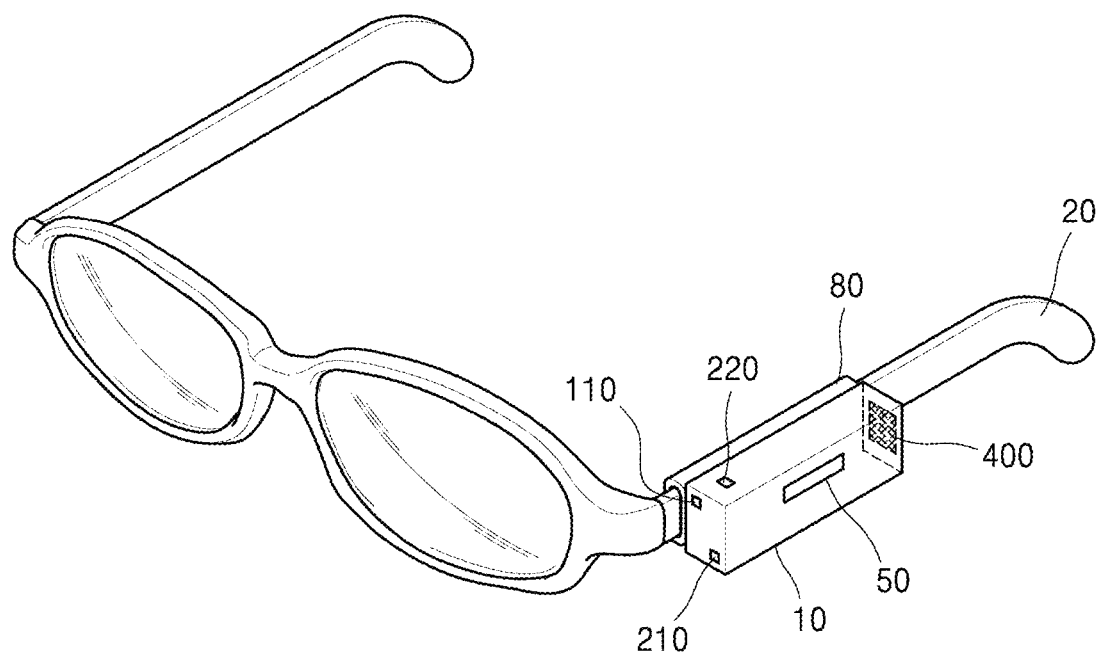
FIG. 3 is an exemplary view illustrating a state in which a pack-type vision assistance apparatus according to an embodiment of the present disclosure is coupled to glasses.
Figure 4A:
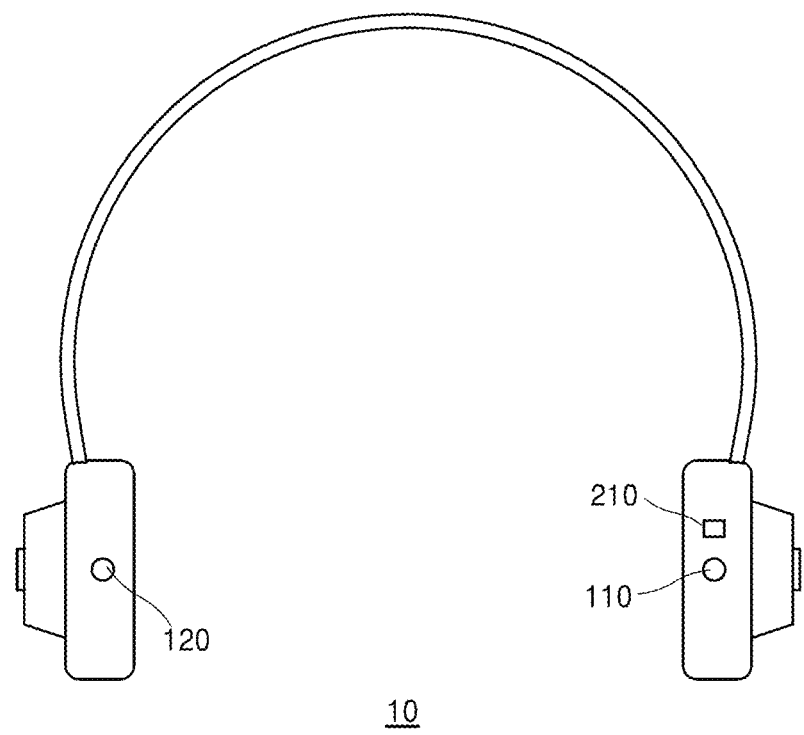
FIG. 4a is a front view illustrating a headset-type vision assistance apparatus according to an embodiment of the present disclosure.
Figure 4B:
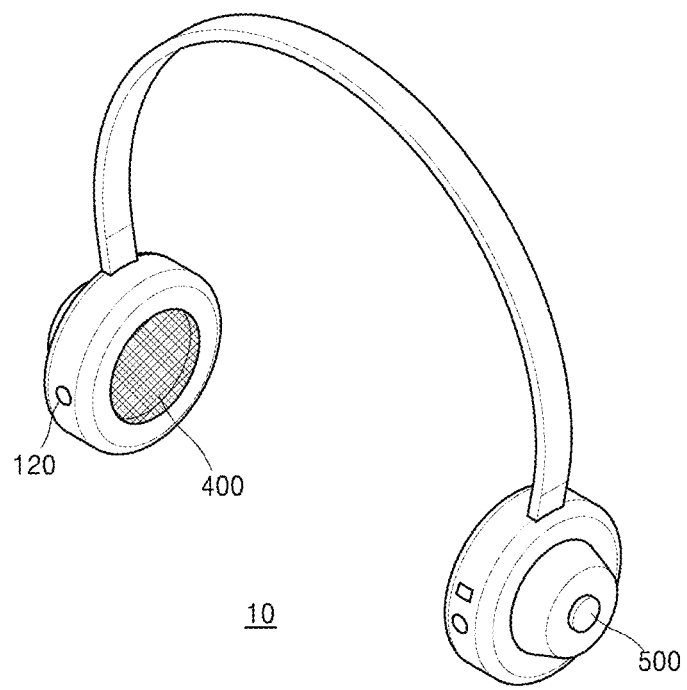
FIG. 4b is a perspective view illustrating the headset-type vision assistance apparatus according to an embodiment of the present disclosure.

FIG. 2 is an exemplary view illustrating a goggle-type vision assistance apparatus 10 according to an embodiment of the present disclosure, FIG. 3 is an exemplary view illustrating a state in which a pack-type vision assistance apparatus 10 according to an embodiment of the present disclosure is coupled to glasses, FIG. 4a is a front view illustrating a headset-type vision assistance apparatus 10 according to an embodiment of the present disclosure, and FIG. 4b is a perspective view illustrating the headset-type vision assistance apparatus 10 according to an embodiment of the present disclosure.

The vision assistance apparatus 10 according to an embodiment of the present disclosure may be provided in various forms as illustrated in FIG. 2, FIG. 3, FIG. 4a, and FIG. 4b. That is, the vision assistance apparatus 10 may be provided in the form of ordinary glasses or goggles as illustrated in FIG. 2, may be modularized as illustrated in FIG. 3 and provided in a form that may be attached/detached to/from ordinary glasses or goggles, or may be provided in the form of a headset as illustrated in FIG. 4a and FIG. 4b. In addition, the vision assistance apparatus 10 may be provided in a form that is attached to the user, such as an earring, a headband, and a necklace, or may be attached to an item of the user, and may be provided in any form as long as it may assist the vision of the user, such as a form that may be grasped by the user.

First, the goggle-type vision assistance apparatus 10 of FIG. 2 according to an embodiment of the present disclosure will be described. A first capturing module 110 for acquiring an image of the front which the left eye of the user watches, the object detection module 210 for detecting an object in front of the user, and the location measurement module 220 for measuring the location of the user may be located at the left upper end of the goggle of the vision assistance apparatus 10, and a second capturing module 120 for acquiring an image of the front which the right eye of the user watches and the distance measurement module 230 for measuring a distance to the object located in front of the user may be located at the right upper end of the goggle of the vision assistance apparatus 10. Furthermore, when the user wears the goggle-type vision assistance apparatus 10 of FIG. 2, the output unit 400, which provides the user with the notification signal in the form of sound, may be located around the ear of the user. When the user wears the goggle-type vision assistance apparatus 10, the output unit 400 may be located only at any one of the left ear and the right ear of the user, but may also be located at either ear of the user. However, the glasses or goggle-type vision assistance apparatus 10 of FIG. 2 is only an exemplary example, and the arrangement of the capturing modules and the arrangement of the sensor modules such as the object detection module 210, the location measurement module 220, and the distance measurement module 230 may be varied for the vision assistance for the user. Furthermore, the type of the goggle itself may also be formed in various forms unlike the vision assistance apparatus 10 of FIG. 2.

Furthermore, the pack-type vision assistance apparatus 10 of FIG. 3 according to an embodiment of the present disclosure will be described. The components of the vision assistance apparatus 10 for vision assistance for the user, such as the first capturing module 110, the object detection module 210, the location measurement module 220, and the output unit 400, are modularized and formed in a rectangular module. However, the pack-type vision assistance apparatus 10 of FIG. 3 is only an exemplary example, and the arrangement of the components of the vision assistance apparatus 10, such as the capturing modules and the sensor modules, may be changed. Furthermore, in FIG. 3, the pack-type vision assistance apparatus 10 is mounted on only one frame 20 of the glasses through a fastening member 800, but unlike this, it may be mounted on either frame 20 thereof. In addition, the pack-type vision assistance apparatus 10 may be provided in any form as long as it is mounted on glasses, or attached to a user's body or item in the form of a module to assist the user's vision.

The vision assistance apparatus 10 according to an embodiment of the present disclosure may also be provided in the form of a headset as illustrated in FIG. 4. Such a headset-type vision assistance apparatus 10 may be formed such that the first capturing module 110, the second capturing module 120, the object detection module 210, and the output unit 400 are modularized to be located around the ears of the user when the user wears the headset-type vision assistance apparatus 10. That is, when the user wears the headset-type vision assistance apparatus 10 as illustrated in FIG. 4a, the first capturing module 110 and the second capturing module 120 are formed toward the front of the headset so as to capture the scene in front of the user. However, since this is only an exemplary example, the first capturing module 110 and the second capturing module 120 may be formed by being attached to a headset in any form as long as it may capture the scene in front of the user. Likewise, the object detection module 210 is formed toward the front of the headset so as to detect an object in front of the user; however, the object detection module 210 may be formed by being located on the headset in any form as long as it may detect an object in front of the user. FIG. 4b is a perspective view illustrating the headset-type vision assistance apparatus 10, which may be formed in a structure in which when the user wears the headset-type vision assistance apparatus 10, the output unit 400 may come into direct contact with the ear of the user. However, this is only an exemplary example, and the headset shape may be formed in various forms unlike FIG. 4a and FIG. 4b.

Figure 5A:
FIG. 5a is a view illustrating an image captured by an image acquisition unit of the vision assistance apparatus according to an embodiment of the present disclosure.
Figure 5B:
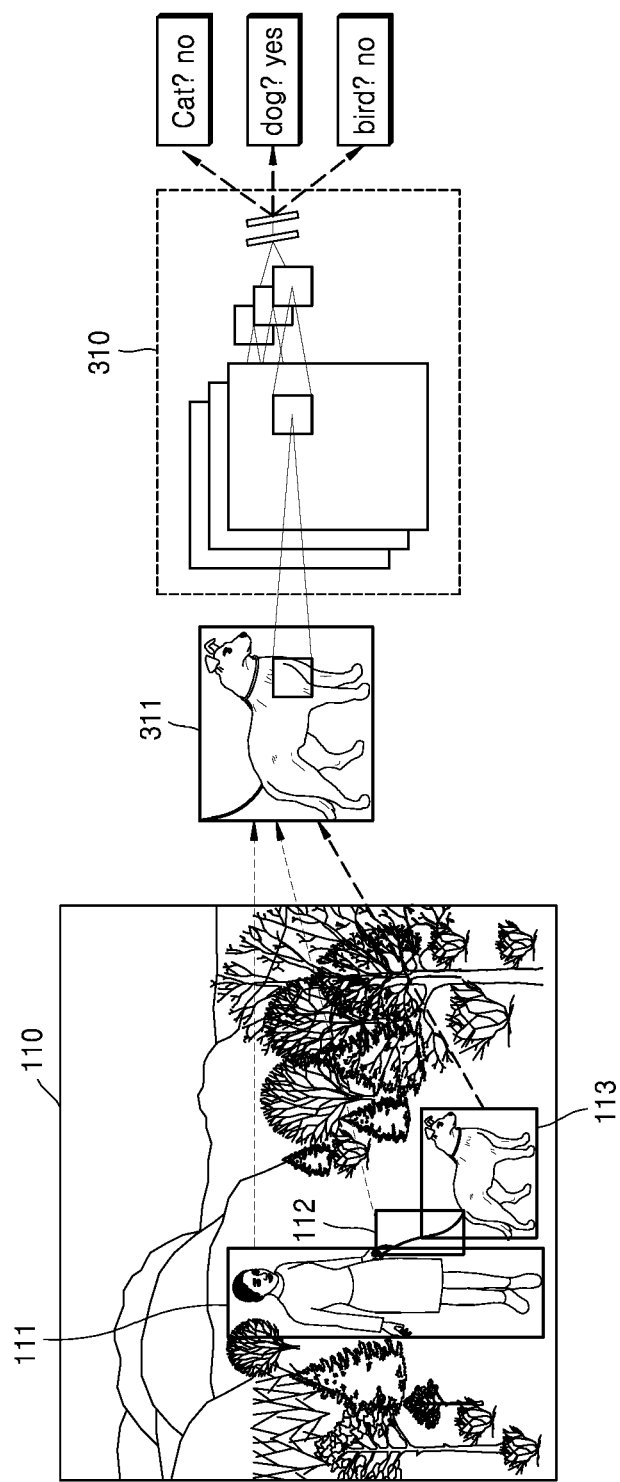
FIG. 5b is an exemplary view illustrating that the image captured by the image acquisition unit of the vision assistance apparatus according to an embodiment of the present disclosure is analyzed by a control unit.

FIG. 5a is a view illustrating an image captured by the image acquisition unit 100 of the vision assistance apparatus 10 according to an embodiment of the present disclosure, and FIG. 5b is an exemplary view illustrating that the image captured by the image acquisition unit 100 of the vision assistance apparatus 10 according to an embodiment of the present disclosure is analyzed by the control unit 300.

Hereinafter, with reference to FIG. 5a and FIG. 5b, the following description will be given for a case where the control unit 300 of the vision assistance apparatus 10 according to an embodiment of the present disclosure executes the learning model and analyzes the acquired image to classify the objects in front of the user, thereby providing vision assistance for the user.

The image analysis by the control unit 300 may be performed through an image learning model, and such a learning model may be a model based on a machine learning or deep learning algorithm. The machine learning or deep learning algorithm-based learning model may be a model obtained or trained using previously acquired learning data (training set).

The control unit 300 of the vision assistance apparatus 10 according to an embodiment of the present disclosure may classify locations and types of the objects in the acquired image. To this end, the learning model executed by the control unit 300 may include regions with convolutional neural network (R-CNN), a fast R-CNN, a faster R-CNN, and a mask R-CNN among deep learning models for classifying objects in an image.

It can be seen in FIG. 5a that in the image captured by the image acquisition unit 100, a woman is talking a walk in a park with a dog on a leash. Hereinafter, with reference to FIG. 5b, the following description will be given for a case where the image of FIG. 5a is analyzed through the R-CNN-based learning model and objects in the image are classified into the woman, the dog, and the leash.

First, as illustrated in a bounding box setting image 130 of FIG. 5b, bounding boxes may be set for the objects in the image captured by the image acquisition unit 100. In order to set such bounding boxes, a selective search algorithm may be used. In such a selective search algorithm, the bounding boxes may be set in a manner that adjacent pixels with similar image color or intensity pattern and the like in an image are combined. In the image, as illustrated in the bounding box setting image 130 of FIG. 5b, a woman bounding box 111 for the woman, a leash bounding box 112 for the leash, and a dog bounding box 113 for the dog may be set.

After the bounding boxes are set, the sizes of the set bounding boxes are unified so that the bounding boxes may be inputted to a convolutional neural network 310. A unified image 311 can be seen in FIG. 5b in which the size of the set dog bounding box 113 has been changed to a predetermined size. The predetermined size may be set in consideration of the number of set bounding boxes, a convolutional neural network model, and the like.

When the sizes of the set bounding boxes are unified, the unified image 311 is inputted to the convolutional neural network 310, and spatial features in the unified image 311 may be extracted through a convolutional layer, a max-pooling layer, and a fully connected layer in the convolutional neural network 310.

Finally, the unified image 311 may be classified through the extracted features by using a support vector machine, so that the objects in the image may be classified. It can be seen in FIG. 5b that the unified image 311 inputted to the convolutional neural network 310 is classified as the dog.

In addition, a pre-processing technique may be performed in advance in order to detect the objects in the image. The pre-processing technique may include any technique capable of more easily performing object detection within an image, such as a technique for converting a captured image into a gray scale image and a binary image.

Figure 6:
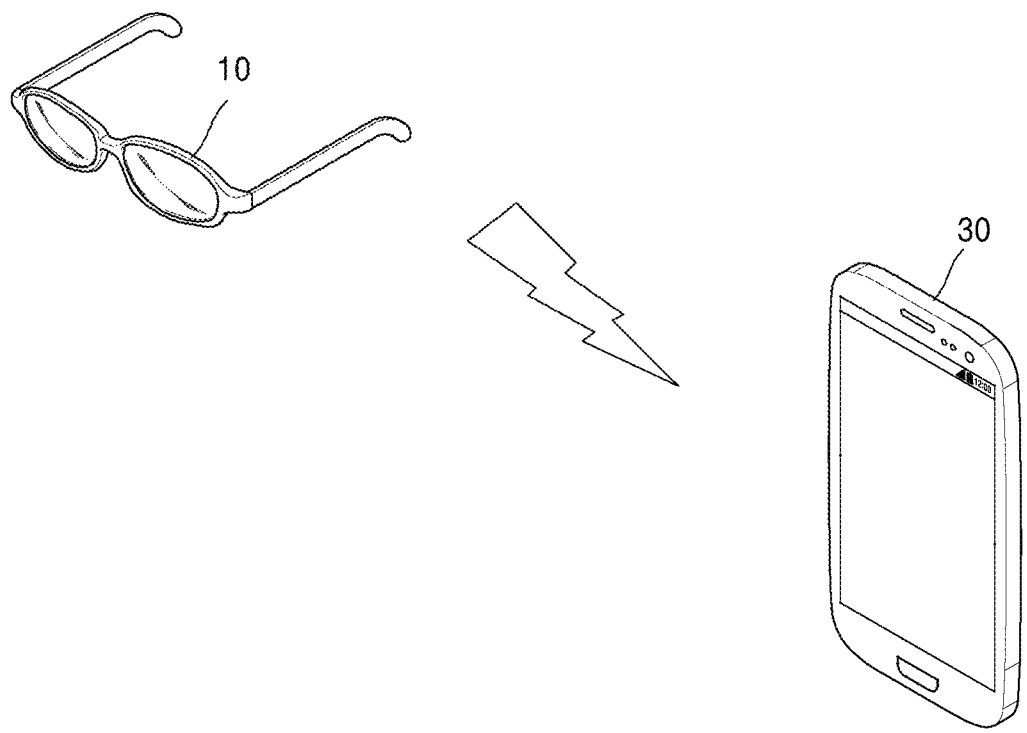
FIG. 6 is an exemplary view illustrating that the vision assistance apparatus according to an embodiment of the present disclosure cooperates with a user device.

The vision assistance apparatus 10 according to an embodiment of the present disclosure may cooperate with the user device 30 as illustrated in FIG. 6. There is no limitation in the user device 30 as long as the user may assist his/her vision in cooperation with the vision assistance apparatus 10 by using the user device 30 such as a smart phone, a cellular phone, a PDA, and a tablet PC.

Furthermore, the vision assistance apparatus 10 according to an embodiment of the present disclosure may include the communication unit 600 in order to cooperate with the user device 30. The communication unit 600 is a component for transmitting or receiving various data to/from the user device 30. Specifically, the communication unit 600 may adjust the supply of power to the vision assistance apparatus 10 through the user device 30. Furthermore, the communication unit 600 may control the operation of the image acquisition unit 100 in the vision assistance apparatus 10 through the user device 30. In addition, the communication unit 600 may receive signals for operations of various components in the vision assistance apparatus 10 from the user device 30, or transmit signals related to operation states of various components in the vision assistance apparatus 10 to the user device 30.

Meanwhile, the communication unit 600 may include various wireless communication modules capable of wirelessly exchanging data with the user device 30. For example, the communication unit 600 may include wireless communication modules based on various communication methods such as Bluetooth, wireless fidelity (WiFi), near field communication (NFC), and long term evolution (LTE).

Figure 7:
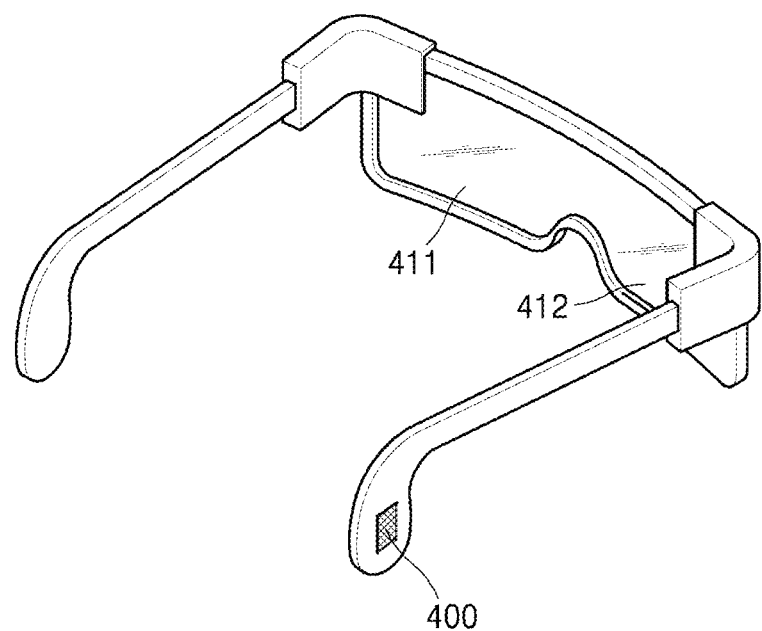
FIG. 7 is an exemplary view illustrating a rear view of the vision assistance apparatus including a display unit according to an embodiment of the present disclosure.

The vision assistance apparatus 10 according to an embodiment of the present disclosure may include a display unit as illustrated in FIG. 7. As illustrated in FIG. 7, the display unit may be composed of a first display unit 411 for the left eye and a second display unit 412 for the right eye. Furthermore, unlike this, the display unit may be formed as a single display panel. The display unit may be implemented with various display devices such as a liquid crystal display (LCD), a light emitting diode (LED), and an organic light emitting diode (OLED). Preferably, the display unit may be implemented with a transparent organic light emitting diode element.

Meanwhile, the display unit may output an auxiliary image for vision assistance for the user by correcting the image acquired by the image acquisition unit 100. The display unit may include an image processing module for correcting the image acquired by the image acquisition unit 100. Any image correction method for generating the auxiliary image for vision assistance for the user, such as converting the color of image data and expanding and reducing of the image data, may be applied to the image correction by the image processing module.

The vision assistance apparatus 10 according to an embodiment of the present disclosure may further include a mode selection unit 500 for selecting an operation mode according to the user. The mode selection unit 500 may be attached to the vision assistance apparatus 10 in the form of a button or a switch, so that the operation mode may be selected by the user. Furthermore, the mode selection unit 500 may be provided with a touch detection sensor module using a capacitive touch sensor or a resistive touch sensor, so that the operation mode may be selected through a user's touch.

The mode selection unit 500 according to the type of the vision assistance apparatus 10 will be described. In the case of the goggle-type vision assistance apparatus 10 according to an embodiment of the present disclosure, the mode selection unit 500 may be provided on the left frame 20 as illustrated in FIG. 2. Furthermore, in the case of the pack-type vision assistance apparatus 10 according to an embodiment of the present disclosure, the mode selection unit 500 may be provided on the side of the pack as illustrated in FIG. 3. In addition, in the case of the headset-type vision assistance apparatus 10 according to an embodiment of the present disclosure, the mode selection unit 500 may be located on the side of the headset as illustrated in FIG. 4a and FIG. 4b. However, the mode selection unit 500 provided in such a vision assistance apparatus 10 may be formed in various forms, and the form thereof is not limited to the forms of the mode selection unit 500 illustrated in FIG. 2, FIG. 3, FIG. 4a, and FIG. 4b.

Figure 8:
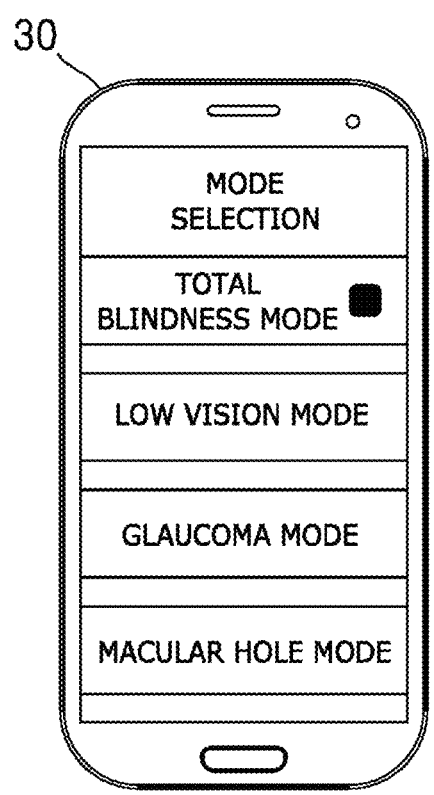
FIG. 8 is an exemplary view illustrating that an operation mode of the vision assistance apparatus according to an embodiment of the present disclosure is selected through the user device.

Unlike the mode selection unit provided with the button and the sensor in the vision assistance apparatus 10 as illustrated in FIG. 2, FIG. 3, FIG. 4a, and FIG. 4b, the operation mode of the vision assistance apparatus 10 according to an embodiment of the present disclosure may be selected through the user device 30 as illustrated in FIG. 8. That is, the user may select the operation mode of the vision assistance apparatus 10 through manipulation of the user device 30 such as touching a screen of the user device 30 and pressing a button provided in the user device 30.

The operation mode of the vision assistance apparatus 10 may include a total blindness mode, a low vision mode, a glaucoma mode, a macular hole mode, a strabismus mode, and an auditory assistance mode. In addition, the operation mode may include various operation modes for vision assistance for the user according to the type of visual impairment or the type of eye disease.

First, the total blindness mode, which is an operation mode applicable when the user is total blind, will be described.

The total blindness refers to a state in which visual ability is lost due to an abnormality in the eye or a neurological cause, and refers to a state in which it is not possible to discriminate an object through the eye. When the user is total blind, the user may not receive vision assistance even though an auxiliary image is outputted through the display unit of the vision assistance apparatus 10.

Accordingly, in the vision assistance apparatus 10 according to an embodiment of the present disclosure, in a case where the total blindness mode is selected as the operation mode because the user is total blind, vision assistance may be performed by a method of providing the user with the notification signal in the form of sound.

A case where the goggle-type vision assistance apparatus 10 of FIG. 2 operates in the total blindness mode will be described. A method in which the notification signal is provided using the object detection module 210, the location measurement module 220, and the distance measurement module 230 attached to the vision assistance apparatus 10 may be performed.

Specifically, the object in front of the user may be detected by the object detection module 210, and a distance from the user to the object may be measured through the distance measurement module 230. In such a case, the control unit 300 may allow the notification signal to be provided only when it is determined that the measured distance is within a predetermined reference value. Furthermore, the control unit 300 may allow the capturing module of the image acquisition unit 100 to operate only when it is determined that the measured distance from the user to the object is within the predetermined reference value. In addition, when the distance from the user to the object is larger than the predetermined reference value, the notification signal may be provided based on only a current location of the user measured through the location measurement module 220.

For example, a case where a pedestrian is walking in front of the user toward the user while the user is walking will be described. The object detection module 210 of the vision assistance apparatus 10 may detect the pedestrian in front of the user as an object, and the distance measurement module 230 may determine that a distance from the user to the pedestrian is within 2 meters. In such a case, the image acquisition unit 100 may acquire an image by capturing the scene in front of the user, and the captured image may be analyzed by the control unit 300 and the pedestrian may be classified as an object. Thus, the notification signal indicating that the pedestrian is walking toward the user is provided to the user in the form of sound, so that vision assistance for the user may be provided.

That is, it may be determined that a sensing signal for the object in front of the user is detected by the sensor unit 200 and the image acquired by the image acquisition unit 100 needs to be analyzed. Accordingly, the image may be analyzed by the control unit 300 and the notification signal for vision assistance for the user may be provided in the form of sound.

In addition, the volume, language and the like of the notification signal provided in the form of sound may be adjusted through a first adjustment unit 521 and a second adjustment unit 522 in FIG. 2. Thus, the user may adjust the notification signal of the vision assistance apparatus 10, so that vision assistance for the user may be provided.

When the user does not have the total blind but has a low vision, the vision assistance apparatus 10 may operate in the low vision mode. Hereinafter, a case where the low vision mode is selected as the operation mode of the vision assistance apparatus 10 will be described.

The person with low vision is not total blind, but may dimly recognize an object. As in the case of the total blind person, vision assistance may be provided for the person with low vision through the notification signal provided in the form of sound, but it may be more effective that vision assistance is performed to allow the person with low vision to be able to directly recognize an object through his/her own eyes.

Accordingly, for vision assistance for the person with low vision, an auxiliary image may be generated and outputted differently depending on the degree of vision or the degree of visual impairment of the user. To this end, when the vision assistance apparatus 10 operates in the low vision mode, the degree and type of the visual impairment of the user may be inputted through the user device 30. The display unit of the vision assistance apparatus 10 may adjust at least one of contrast data, color data, focus data, brightness data, and size data of the acquired image according to the degree and type of the visual impairment of the user inputted through the user device 30, and generate and output an auxiliary image.

Furthermore, in the goggle-type vision assistance apparatus 10 of FIG. 2 according to an embodiment of the present disclosure, the first adjustment unit 521 and the second adjustment unit 522 may be provided on one side of the frame 20. The first adjustment unit 521 and the second adjustment unit 522 may allow the user to perform at least one of expansion and reduction, color adjustment, focus adjustment, and brightness adjustment of the auxiliary image. That is, even in the auxiliary image generated through this, the image may be adjusted according to the current situation of the user, so that vision assistance for the user may be provided.

When the user has a glaucoma disease, the vision assistance apparatus 10 may operate in the glaucoma mode. Hereinafter, a case where the glaucoma mode is selected as the operation mode of the vision assistance apparatus 10 will be described.

The glaucoma refers to a state in which an optic nerve is damaged due to an increase in intraocular pressure, and the like and the visual field is narrowed. A patient with glaucoma may have visual field defects and a patient with terminal glaucoma may have tunnel vision. The tunnel vision may be formed in a tunnel shape in which the vision becomes darker as the distance from the center of the vision increases.

Figure 9:
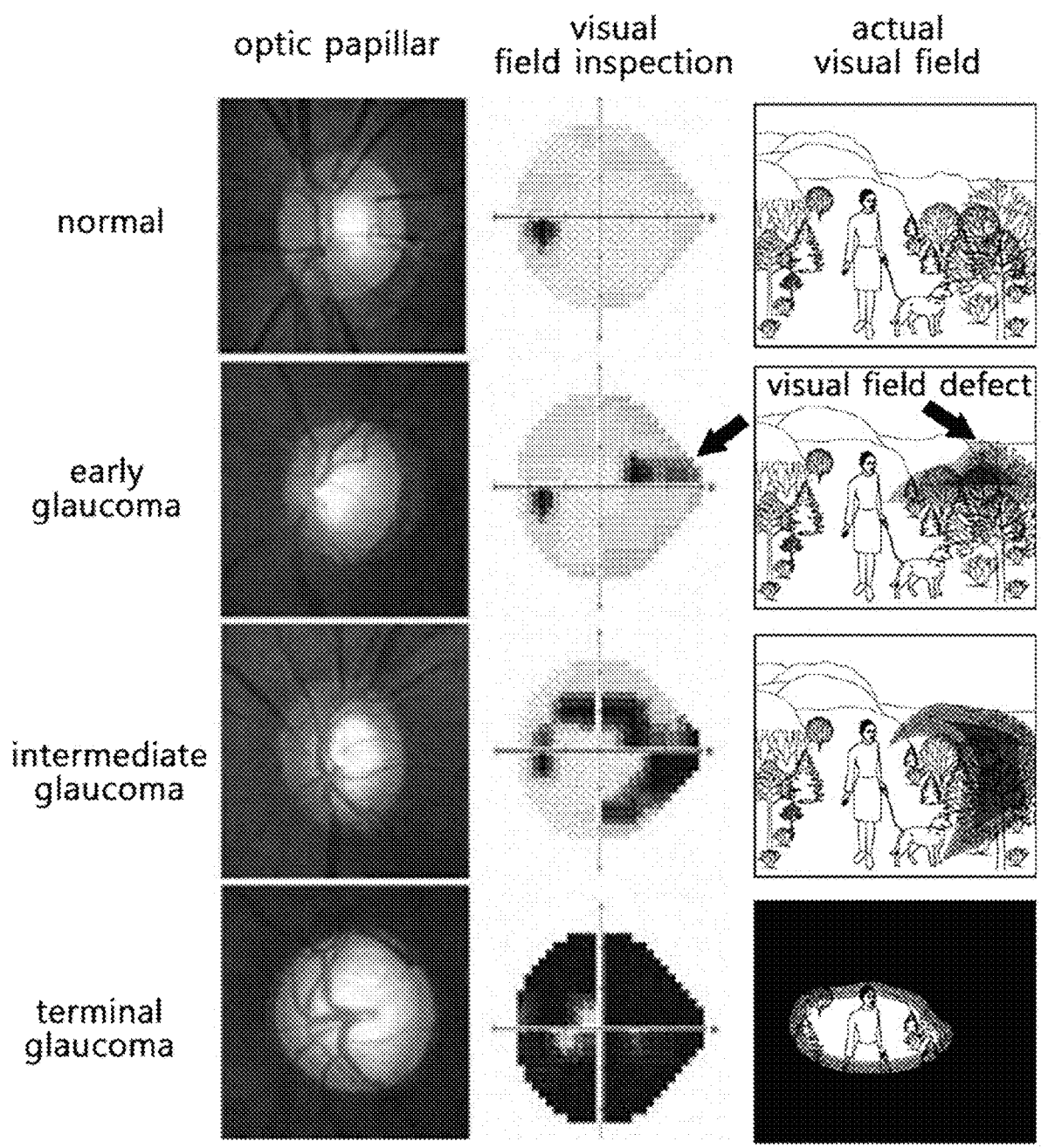
FIG. 9 is an exemplary view illustrating a visual field according to the degree of progress of a user's glaucoma.

The user's vision according to the degree of progress of the glaucoma may be classified as at least any one of normal, early glaucoma, intermediate glaucoma, and terminal glaucoma as illustrated in FIG. 9. That is, a patient with early glaucoma may have dark spots to cause visual field defects, a patient with intermediate glaucoma may have the dark spots which become darker or enlarged, and a patient with terminal glaucoma may have tunnel vision due to the enlarged dark spots. However, the figures for vision caused due to the glaucoma in FIG. 9 is for illustrative purposes only, and when the locations of the dark spot and the tunnel vision of the patient with glaucoma are changed or even when the degree of darkening of the dark spot or the degree of darkness of the tunnel vision is changed, vision assistance for the user may be provided by the glaucoma mode of the vision assistance apparatus 10 according to an embodiment of the present disclosure.

When the vision assistance apparatus 10 according to an embodiment of the present disclosure operates in the glaucoma mode, the capturing module of the image acquisition unit 100 may include a fish-eye lens. That is, the image acquisition unit 100 may acquire a fish-eye image 534 captured by the fish-eye lens camera. The display unit may output an auxiliary image formed by remapping the acquired fish-eye image 534 into the tunnel vision of the user.

Specifically, when the patient with glaucoma has the tunnel vision as illustrated in FIG. 9, it may be difficult for the user to properly recognize the scene in the visual field in front of the user. That is, the user may recognize only the upper body of the woman or may not recognize surrounding objects because the rest of the user's visual field is narrowed. Referring to FIG. 10, a wide visual field may be secured through the fish-eye image 534 captured by the image acquisition unit 100 of the vision assistance apparatus 10 according to an embodiment of the present disclosure, and a remapped image 535 in which such a fish-eye image 534 is remapped into the tunnel vision of the user may be formed. That is, as in the remapped image 535 of FIG. 10, the fish-eye image 534, in which the woman and the dog are together in the park, is remapped into the tunnel vision, so that the user may check that the woman and the dog are in the park.

When the user has a macular hole disease, the vision assistance apparatus 10 may operate in the macular hole mode. Hereinafter, a case where the macular hole mode is selected as the operation mode of the vision assistance apparatus 10 will be described.

Figure 11:
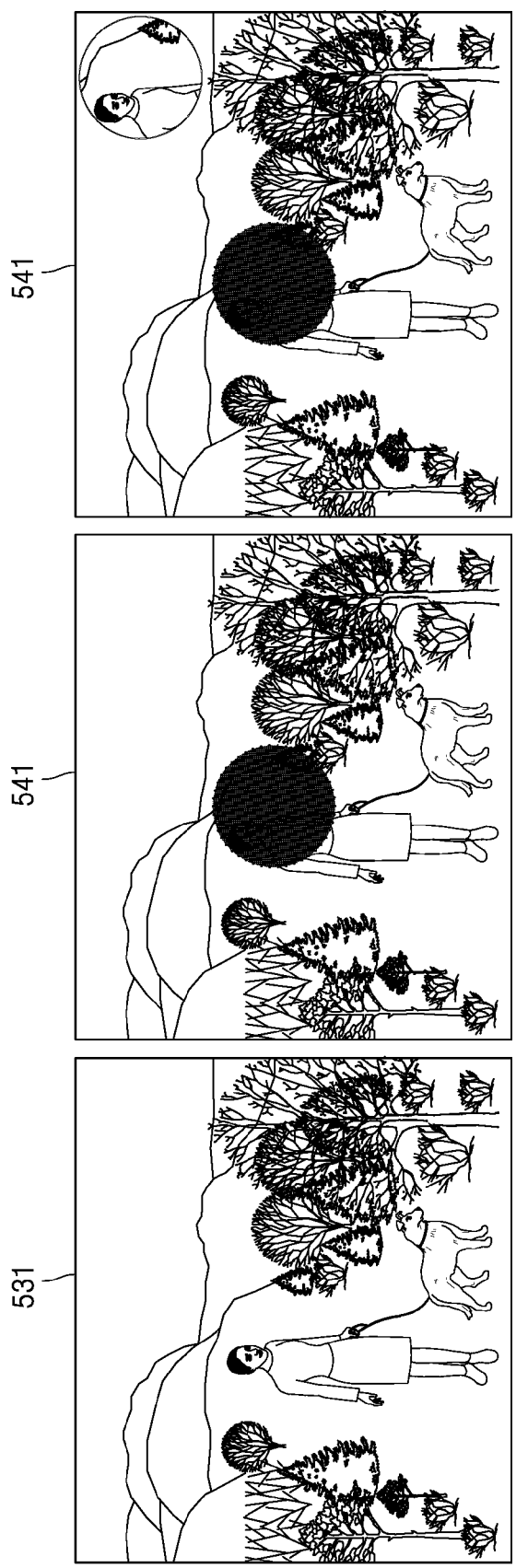
FIG. 11 is an exemplary view illustrating that a missing visual field of a user is separately displayed when the vision assistance apparatus according to an embodiment of the present disclosure operates in a macular hole mode.

The macular hole refers to a state in which the entire layer or a part of the macular retina has been lost. A patient with macular hole may have vision loss in the center of the visual field and dark spots generated in the center of the visual field. Referring to FIG. 11, it can be seen that vision loss occurs in the center of the visual field 541 of the macular hole and the visual field for the upper body of the woman is lost unlike a normal visual field 531.

When the vision assistance apparatus 10 according to an embodiment of the present disclosure operates in the macular hole mode, the display unit may output an auxiliary image formed by allowing a part deficient due to a dark spot generated in the center of the visual field of the user to be separately displayed on a peripheral part adjacent to the center of the visual field of the user. That is, as illustrated in FIG. 11, an image on the upper body of the woman lost in the normal visual field 531 is separately displayed on the upper right end of a macular hole correction image 542, so that vision assistance for the user may be provided. Accordingly, the user may check the lost visual field in the peripheral part of the correction image, thereby accurately acquiring information on the scene in front of the user.

When the user is a patient with strabismus, the vision assistance apparatus 10 may operate in the strabismus mode. Hereinafter, a case where the strabismus mode is selected as the operation mode of the vision assistance apparatus 10 will be described.

The strabismus refers to a visual impairment in which two eyes are not aligned and look at different points. In the case of the strabismus, vision assistance may be provided by adjusting a difference between viewing angles that occur when the left eye and the right eye are not aligned. Accordingly, auxiliary images for the left eye and the right eye are differently formed by shifting the image acquired by the image acquisition unit 100 such that the difference between viewing angles is adjusted, so that vision assistance may be provided.

The vision assistance apparatus 10 according to an embodiment of the present disclosure may generate a first auxiliary image and a second auxiliary image by shifting the image acquired by the image acquisition unit 100, on the basis of the viewing angle of the left eye and the viewing angle of the right eye. That is, the first auxiliary image and the second auxiliary image generated through the image shifting may be outputted to the first display unit 411 for the left eye and the second display unit 412 for the right eye, respectively, so that vision assistance for the user with strabismus may be provided.

When the user has a hearing impairment, the vision assistance apparatus 10 may operate in the auditory assistance mode. However, the vision assistance apparatus 10 may operate in the auditory assistance mode only in the case of the other visual impairments except for the case of total blindness in which a user completely loses his/her vision. That is, in the case of a person with low vision, a patient with glaucoma, a patient with macular hole, and a patient with strabismus and a hearing impairment, both auditory assistance and vision assistance may be provided through the output of an auxiliary image.

When the vision assistance apparatus 10 according to an embodiment of the present disclosure operates in the auditory assistance mode, the control unit 300 may generate an image signal for the object by analyzing sound information from the object acquired by the sensor unit 200. Then, an auxiliary image formed by allowing the image signal generated by the control unit 300 to be displayed on the image captured by the image acquisition unit 100 may be outputted through the display unit, so that auditory assistance may be provided. In such a case, the sensor unit 200 may include a sound input section for inputting a sound of the object.

Specifically, auditory assistance for the user will be described with reference to FIG. 12. When the barking sound of the dog is inputted to the sound input section of the sensor unit 200, the control unit 300 may analyze the inputted sound to generate an image signal for the object. That is, the control unit 300 may analyze the barking sound of the dog to generate an image signal such as "dog barking sound" of FIG. 12. Then, an auxiliary image such as a first auditory auxiliary image 561 of FIG. 12, in which such an image signal is displayed on the acquired image by the display unit, may be generated and outputted.

Figure 12:
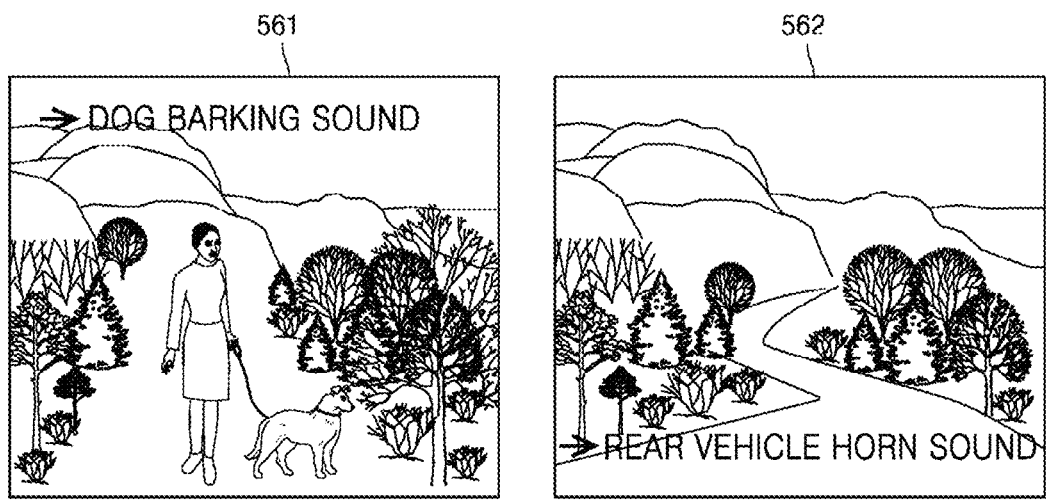
FIG. 12 is an exemplary view illustrating that an image signal is generated on a display unit when the vision assistance apparatus according to an embodiment of the present disclosure operates in an auditory assistance mode.

Furthermore, referring to FIG. 12, when the horn sound of a vehicle is inputted to the sound input section of the sensor unit 200, the control unit 300 may also consider a direction in which the inputted sound is transmitted. Accordingly, the control unit 300 may analyze the inputted sound to generate an image signal indicating the horn sound from a rear vehicle. As a consequence, the user may check an auxiliary image such as a second auditory auxiliary image 562 in which the image signal indicating "rear vehicle horn sound" is displayed on the image acquired by the image acquisition unit 100.

In addition, in the case of the other visual impairments except for the case of total blindness in which a user completely loses his/her vision, the vision assistance apparatus 10 may operate in another operation mode together with the auditory assistance mode. Specifically, when the user has a low vision, an auxiliary image may be first generated by correcting the image acquired by the image acquisition unit 100. Then, an image signal may be generated by analyzing sound information acquired by the sound input section of the sensor unit 200. As a consequence, an image, in which the image signal is combined with the auxiliary image, may be outputted to the display unit for the user, so that both vision assistance and auditory assistance may be provided for the user.

Figure 13:
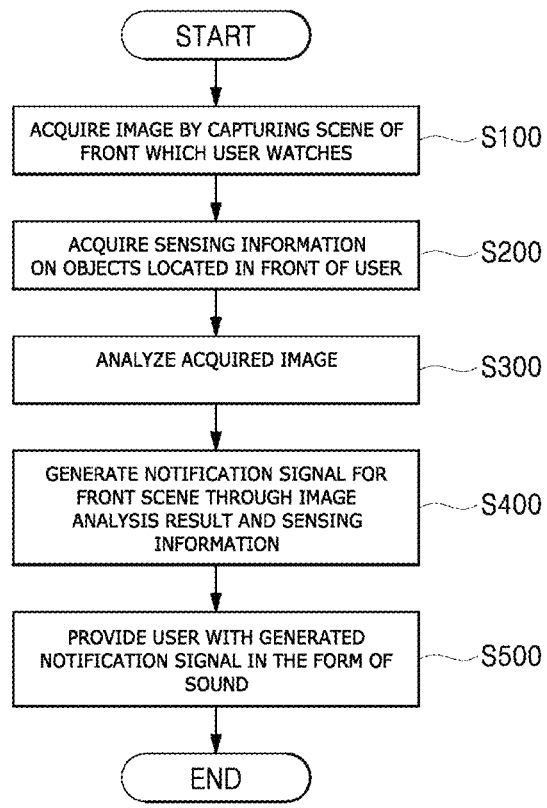
FIG. 13 is a flowchart illustrating a vision assistance method for a user using the vision assistance apparatus according to an embodiment of the present disclosure.

FIG. 13 is a flowchart illustrating a vision assistance method for a user using the vision assistance apparatus 10 according to an embodiment of the present disclosure.

Referring to FIG. 13, the vision assistance method for a user using the vision assistance apparatus 10 according to an embodiment of the present disclosure may include a step S100 of acquiring an image by capturing the scene of the front which a user watches, a step S200 of acquiring sensing information on objects located in front of the user, a step S300 of analyzing the acquired image, a step S400 of generating a notification signal for the front scene through an analysis result of the acquired image and the acquired sensing information, and a step S500 of providing the user with the generated notification signal in the form of sound.

Figure 14:
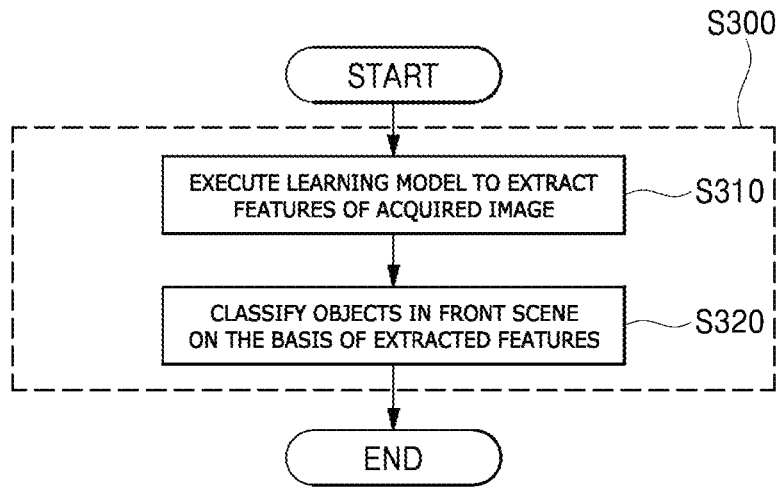
FIG. 14 is a flowchart illustrating an exemplary process in which the vision assistance apparatus according to an embodiment of the present disclosure analyzes an image.

FIG. 14 is a flowchart illustrating an exemplary process in which the vision assistance apparatus 10 according to an embodiment of the present disclosure analyzes the image.

Referring to FIG. 14, the step S300, in which the vision assistance apparatus 10 according to an embodiment of the present disclosure analyzes the image, may include a step S310 of executing a learning model to extract features of the acquired image and a step S320 of classifying objects in the front scene on the basis of the extracted features.

Figure 15:
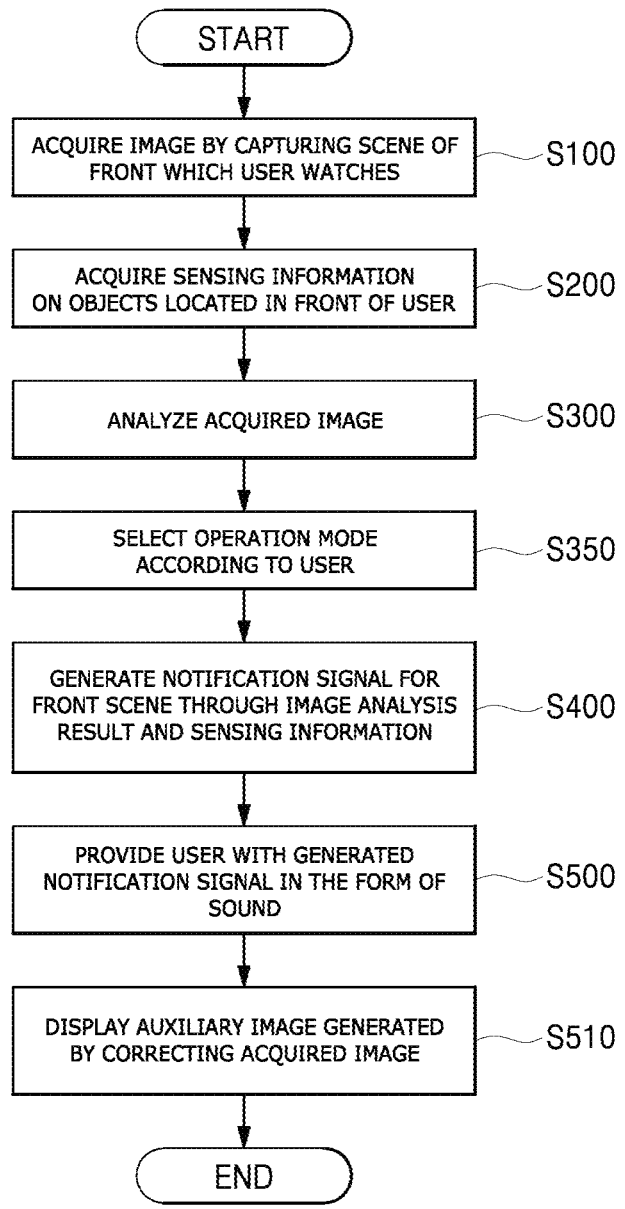
FIG. 15 is a flowchart illustrating an exemplary process in which the vision assistance apparatus according to an embodiment of the present disclosure displays an auxiliary image.

FIG. 15 is a flowchart illustrating an exemplary process in which the vision assistance apparatus 10 according to an embodiment of the present disclosure displays the auxiliary image.

Referring to FIG. 15, the vision assistance method for a user using the vision assistance apparatus 10 according to an embodiment of the present disclosure may include the step S100 of acquiring an image by capturing the scene of the front which a user watches, the step S200 of acquiring sensing information on objects located in front of the user, the step S300 of analyzing the acquired image, a step S350 of selecting an operation mode according to the user, the step S400 of generating a notification signal for the front scene through an analysis result of the acquired image and the acquired sensing information, the step S500 of providing the user with the generated notification signal in the form of sound, and a step S510 of displaying an auxiliary image generated by correcting the acquired image.

Meanwhile, the aforementioned method may be written as a program executable in a computer and may be implemented in a general-purpose digital computer that executes the program using a computer-readable medium. Furthermore, the structure of data used in the aforementioned method may be recorded on the computer-readable medium through various means. It should not be understood that a recording medium for recording executable computer programs or codes for performing various methods of the present disclosure includes temporary objects such as carrier waves or signals. The computer-readable medium may include a storage medium such as a magnetic storage medium (for example, a ROM, a floppy disk, a hard disk, and the like) and an optical reading medium (for example, a CD-ROM, a DVD, and the like).

The aforementioned description of the present disclosure is for illustrative purposes only, and those skill in the art to which the present disclosure pertains will be able to understand that the present disclosure can be easily modified into other specific forms without changing the technical spirit or essential features of the present disclosure. Therefore, it should be understood that the embodiments described above are illustrative in all respects, not limitative. For example, each component described as a single form may be implemented in a distributed manner, and similarly, components described as being distributed may also be implemented in a combined form.

The scope of the present disclosure is defined by the claims to be described below rather than the detailed description, and it should be construed that the meaning and scope of the claims and all modifications or modified forms derived from the equivalent concept thereof are included in the scope of the present disclosure.

The invention claimed is:

1. A vision assistance apparatus comprising:
   an image acquisition unit configured to acquire an image by capturing a scene of a front which a user watches;
   a sensor unit configured to acquire sensing information on objects located in front of the user;
   a control unit configured to analyze the image acquired by the image acquisition unit and generate a notification signal for the front scene through an analysis result of the image and the sensing information acquired by the sensor unit; and
   an output unit configured to provide the user with the notification signal generated by the control unit in a form of sound,
   a display unit configured to output an auxiliary image for vision assistance of the user generated b correcting the image acquired b the image acquisition unit,
   a mode selection unit configured to select an operation mode according to the user,
   wherein the control unit executes a predetermined learning model for extracting features from the acquired image, and analyzes the image by classifying the objects in the front scene on a basis of the features extracted using the learning model, wherein the operation mode includes a glaucoma mode, and when the glaucoma mode is selected as the operation mode,
the image acquisition unit acquires a fish-eye image captured by a fish-eye lens camera, and
the display unit outputs the auxiliary image formed by remapping the fish-eye image into tunnel vision of the user.

2. The vision assistance apparatus according to claim 1, wherein the operation mode includes a total blindness mode, and in a case where the total blindness mode is selected as the operation mode,
the sensor unit measures a distance value from the object to the user, and when the control unit determines that the measured distance value is within a predetermined reference value, the notification signal is outputted through the output unit.

3. The vision assistance apparatus according to claim 1, wherein the operation mode includes a low vision mode, and when the low vision mode is selected as the operation mode,
the display unit outputs the auxiliary image generated by adjusting at least one of contrast data, color data, focus data, brightness data, and size data of the acquired image.

4. A vision assistance apparatus comprising:
an image acquisition unit configured to acquire an image by capturing a scene of a front which a user watches;
a sensor unit configured to acquire sensing information on objects located in front of the user;
a control unit configured to analyze the image acquired by the image acquisition unit and generate a notification signal for the front scene through an analysis result of the image and the sensing information acquired by the sensor unit; and
an output unit configured to provide the user with the notification signal generated by the control unit in a form of sound,
a display unit configured to output an auxiliary image for vision assistance of the user generated by correcting the image acquired by the image acquisition unit,
a mode selection unit configured to select an operation mode according to the user,
wherein the control unit executes a predetermined learning model for extracting features from the acquired image, and analyzes the image by classifying the objects in the front scene on a basis of the features extracted using the learning model,
wherein the operation mode includes a macular hole mode,
and when the macular hole mode is selected as the operation mode,
the display unit outputs the auxiliary image formed by allowing a part deficient due to a dark spot generated in a center of a visual field of the user to be separately displayed on a peripheral part adjacent to the center of the visual field of the user.

5. A vision assistance apparatus comprising:
an image acquisition unit configured to acquire an image by capturing a scene of a front which a user watches;
a sensor unit configured to acquire sensing information on objects located in front of the user;
a control unit configured to analyze the image acquired by the image acquisition unit and generate a notification signal for the front scene through an analysis result of the image and the sensing information acquired by the sensor unit; and
an output unit configured to provide the user with the notification signal generated by the control unit in a form of sound,
a display unit configured to output an auxiliary image for vision assistance of the user generated by correcting the image acquired by the image acquisition unit,
a mode selection unit configured to select an operation mode according to the user,
wherein the control unit executes a redetermined learning model for extracting features from the acquired image, and analyzes the image by classifying the objects in the front scene on a basis of the features extracted using the learning model,
wherein the operation mode includes a strabismus mode,
and when the strabismus mode is selected as the operation mode,
the auxiliary image includes a first auxiliary image for a left eye of the user and a second auxiliary image for a right eye of the user, and
the display unit outputs the first auxiliary image and the second auxiliary image formed by shifting the image acquired by the image acquisition unit, on the basis of a viewing angle of the left eye of the user and a viewing angle of the right eye of the user.

6. A vision assistance apparatus comprising:
an image acquisition unit configured to acquire an image by capturing a scene of a front which a user watches;
a sensor unit configured to acquire sensing information on objects located in front of the user;
a control unit configured to analyze the image acquired by the image acquisition unit and generate a notification signal for the front scene through an analysis result of the image and the sensing information acquired by the sensor unit; and
an output unit configured to provide the user with the notification signal generated by the control unit in a form of sound,
a display unit configured to output an auxiliary image for vision assistance of the user generated by correcting the image acquired by the image acquisition unit,
a mode selection unit configured to select an operation mode according to the user,
wherein the control unit executes a redetermined learning model for extracting features from the acquired image, and analyzes the image by classifying the objects in the front scene on a basis of the features extracted using the learning model,
wherein the operation mode includes an auditory assistance mode,
and when the auditory assistance mode is selected as the operation mode,
the control unit generates an image signal for the object by analyzing sound information from the object acquired by the sensor unit, and
the auxiliary image formed by allowing the image signal generated by the control unit to be displayed on the image acquired by the image acquisition unit is outputted through the display unit.

7. A vision assistance method of a user using a vision assistance apparatus, the vision assistance method comprising:
a step of acquiring an image by capturing a scene of a front which a user watches;
a step of acquiring sensing information on objects located in front of the user;
a step of analyzing the acquired image;

a step of generating a notification signal for the front scene through an analysis result of the acquired image and the acquired sensing information; and a step of providing the user with the generated notification signal in a form of sound, wherein the step of analyzing the acquired image comprises:

a step of executing a redetermined learning model to extract features of the acquired image; and a step of classifying objects in the front scene on a basis of the extracted features, wherein a step of selecting an operation mode according to the user is performed before execution of the step of generating a notification signal for the front scene through an analysis result of the acquired image and the acquired sensing information, and a step of displaying an auxiliary image for vision assistance for the user, which is generated by correcting the acquired image, is performed together with the step of providing the user with the generated notification signal in the form of sound.

8. A non-transitory computer-readable recording medium storing a program for performing the method according to claim 7.

* * * * *